(12) United States Patent
Perry et al.

(10) Patent No.: US 6,881,569 B2
(45) Date of Patent: Apr. 19, 2005

(54) APPARATUS AND METHOD FOR EVALUATING TISSUE ENGINEERED BIOLOGICAL MATERIAL

(75) Inventors: Tjorvi Ellert Perry, Jamaica Plain, MA (US); Fraser W. H. Sutherland, West Lothian (GB); John E. Mayer, Jr., Wellesley, MA (US)

(73) Assignee: Children's Medical Center Corporation, Boston, MA (US)

( * ) Notice: Subject to any disclaimer, the term of this patent is extended or adjusted under 35 U.S.C. 154(b) by 44 days.

(21) Appl. No.: 10/056,991

(22) Filed: Jan. 25, 2002

(65) Prior Publication Data

US 2003/0143519 A1 Jul. 31, 2003

(51) Int. Cl.[7] ................................................. C12M 3/00
(52) U.S. Cl. ............................. 435/284.1; 435/286.5; 435/293.1; 623/912; 623/915; 623/916
(58) Field of Search .......................... 435/284.1, 286.5, 435/289.1, 293.1; 623/912–923; 73/865.9, 866.4

(56) References Cited

U.S. PATENT DOCUMENTS

| | | | | |
|---|---|---|---|---|
| 3,738,914 A | * | 6/1973 | Thorne et al. ............ | 435/284.1 |
| 5,272,909 A | * | 12/1993 | Nguyen et al. ................ | 73/37 |
| 5,899,937 A | | 5/1999 | Goldstein et al. ............... | 623/2 |
| 5,916,800 A | | 6/1999 | Elizondo et al. .......... | 435/284.1 |
| 6,121,042 A | | 9/2000 | Peterson et al. .......... | 435/284.1 |

OTHER PUBLICATIONS

Fischer et al. "Design of a function test apparatus for prosthetic heart valves." Clin. Phys. Physiol. Meas. vol. 7 (1986), No. 1, pp. 63–73.*

Tindale et al. "In vitro evaluation of prosthetic heart valves: anomalies and limitations." Clin. Phys. Physiol/Meas. vol. 3 (1982) No. 2, pp. 115–130.*

Hoerstrup, et al. (2000), *Tissue Engineering*, vol. 6, No. 1:75–79.

* cited by examiner

*Primary Examiner*—William H. Beisner
(74) *Attorney, Agent, or Firm*—Nixon Peabody LLP

(57) ABSTRACT

An apparatus and method that allows the visualization of leakage of cell culture media through a conduit wall of a tissue-engineered biological construct such as a semilunar heart valve or valve graft under controlled physiologic conditions. The apparatus and method also allows for the assessment of valve function and intraluminal flow using conventional imaging modalities such as ultrasonic and magnetic resonance imaging. The apparatus allows the qualitative and quantitative evaluation of structural and functional characteristics of a condition tissue engineered construct prior to implantation using a valve housing and chamber and a flow-pressure simulator.

2 Claims, 3 Drawing Sheets

APPARATUS AND METHOD FOR EVALUATING TISSUE ENGINEERED BIOLOGICAL MATERIAL

GOVERNMENT SUPPORT

The subject matter of this application was made with support from the United States Government (National Institutes of Health Grant No. 5 RO1 HL 60463-03). The Government has certain in the invention.

FIELD OF THE INVENTION

The present invention is directed generally to a system and method for evaluating laboratory-grown molecules, cells, tissues, or organs to replace or support the function of damaged or defective body parts. More particularly, the present invention is directed to a system that allows the visualization of leakage of cell culture media through the conduit wall of a tissue engineered heart valve or valve graft, evaluation of overall leaflet function, including leaflet excursion and coaptation, and evaluation of flow characteristics under controlled physiologic conditions.

DESCRIPTION OF THE RELATED ART

Tissue engineering is the development and manipulation of laboratory grown molecules, cells, tissues or organs to replace or support the function of defective or injured body parts. Although cells have been cultured, or grown, outside of the body, the possibility of growing complex, three-dimensional tissues, i.e., literally replicating the design and function of human tissue, is a recent development.

There are three general approaches that have been adopted for the creation of new tissue. The first approach involves the design and growth of human tissues outside the body for subsequent implantation to repair or replace diseased tissues. An example of this form of therapy is a skin graft, which is typically used for the treatment of burns. The second approach involves the implantation of cell-containing or cell-free devices which induce the regeneration of functional human tissues. This approach relies on the purification and large-scale production of appropriate "signal" molecules, like growth factors, to assist in biomaterial-guided tissue regeneration. The last approach is the development of external or internal devices containing human tissues designed to replace the function of diseased internal tissues. This approach involves isolating cells from the body, using techniques such as stem cell therapy, placing them on or within structural matrices, and implanting the new system inside the body or using the system outside the body.

Valve disease is a significant cause of morbidity and mortality in the adult and pediatric populations. Currently, mechanical and bioprosthetic devices are used to replace diseased heart valves. The function of the normal heart valve is intimately related to its structure. Manufacturers strive to design heart valves that will function to maximize the effective orifice area while minimizing regurgitant flow, leaflet energy expenditure and abnormal intraluminal flow patterns. Heart valve tissue engineering is a rapidly growing field that may offer an alternative to currently utilized prostheses. Without information detailing the function of the heart valve, however, it will be difficult to take tissue-engineered heart valves into the clinical setting. In designing a tissue-engineered valve, it will be essential to evaluate its function by the same parameters used for mechanical and bioprosthetic devices.

Pulse duplicators are used commercially to test the durability of prosthesis over many cycles. Mechanical and bioprosthetic valves are constructed from non-living components and, for this reason, are different from tissue-engineered valves. Accordingly, this translates into different needs when it concerns testing tissue-engineered valves. Currently, there is no testing system that has been devised to allow the evaluation of the structure and function of a living semilunar valve under sterile conditions. The principle shortcomings of pulse duplicators is that they do not allow for subsequent implantation of the tested prosthesis.

SUMMARY OF THE INVENTION

In view of the foregoing, it is an object of the invention to overcome the disadvantages in the related art in providing an apparatus for housing, supporting and evaluating tissue-engineered biological material.

It is another object of the invention to provide an apparatus composed of a material that can function in a biologic environment without known or significant detrimental effects on the biological material.

It is yet another object of the invention to provide an apparatus that is biomemetic and capable of replicating, simulating or imitating a body function.

It is still further another object of the invention to provide an apparatus that allows the visualization of leakage of cell culture media through the conduit wall of a tissue-engineered biological material such as a heart valve under controlled physiologic conditions.

It is yet another object of the invention to provide an apparatus that allows the assessment of valve function and intraluminal flow using conventional imaging modalities such as ultrasonic and magnetic resonance imaging.

It is yet further another object of the invention to provide an apparatus that allows the qualitative and quantitative evaluation of the structural and functional characteristics of a conditioned tissue-engineered heart valve prior to implantation.

These and other objects are achieved in accordance to a first embodiment of the invention featuring an apparatus for evaluating a structure and function of tissue-engineered construct such as a semilunar valve or vascular graft under sterile conditions prior to in vitro implantation in a ventricular outflow tract. In a preferred embodiment, the apparatus comprises a base for supporting the semilunar valve, the base including a housing-chamber having an inlet port and an outlet port connected to an elastic compliance chamber to allow for radial distention of the tissue engineered construct, a main fluid circuit for allowing flow of a fluid media through said housing, the main fluid circuit being in fluid communication with the housing at the inlet and outlet ports, and a pressure mechanism in fluid communication with the main fluid circuit for generating physiologic flow of the fluid media through the housing at a predetermined pressures.

Also provided is a resistance device in fluid communication with the main fluid circuit for replicating an afterload characteristic, the resistance device being positioned distal to the tissue-engineered construct on an efferent limb of the main circuit. Inn other words, the resistance device generates a resistance counter to the pressure generated by the pressure mechanism at a region distal to the tissue engineered construct. The apparatus further includes a control device in electronic communication with the pressure device for adjustably controlling the predetermined pressure at a level which simulates or replicates intraluminal flow. Such an apparatus is advantageous over those provided in the related art in that the intraluminal flow of the fluid through the main fluid circuit hemodynamically conditions the tissue engineered heart valve prior to in vivo implantation.

Preferably, the main fluid circuit is composed of a rigid material, such as polyvinyl chloride (PVC) tubing, which is in fluid communication with the various components of the apparatus. The apparatus may also include a first auxiliary fluid circuit for bypassing said main fluid circuit to allow for regurgitant flow of said fluid media through said main fluid circuit. The auxiliary circuit may include a check valve for allowing unidirectional flow through the auxiliary fluid circuit. The auxiliary fluid may be composed of a rigid material as the main fluid circuit, in particular, polyvinyl chloride (PVC) tubing. However, the fluid circuits is not limited to polyvinyl chloride (PVC) tubing, and may be composed of any material suitable to the performance of the apparatus.

Preferably, the pressure mechanism is a pump which is in fluid communication with the housing at a region upstream of the housing. Depending on the purpose for creating flow through a tissue engineered heart valve and/or blood vessel, any type of pump can be used, such as a piston-driven pump. However, for this purpose, it is advantageous to use a pump that is capable of most closely simulating in vivo hemodynamic flow and pressure conditions. Hence, it is preferred that a bellows-type fluid pump, such as those produced by Burt Process Equipment, Hamden, Conn., is used to generate the required pressure waveforms to simulate in vivo hemodynamic flow and pressure conditions. A second auxiliary or bypass circuit with a check valve is positioned to bypass the pump and accommodate flow in the opposite direction in the case of regurgitant flow through the tissue-engineered valve. The check valve prevents backflow of the fluid media in the second auxiliary circuit during diastole.

The housing includes an annular chamber and base preferably composed of a transparent material that allows visualization of the tissue-engineered biological material in the test environment. Preferably, the transparent material used for the housing chamber is a clear acrylic, such as the type manufactured by Owl Separating Systems, Inc., Portsmouth, N.H. Clear acrylics have been found to be superior to other transparent materials such as glass and various other plastic material since it allows the capability of visualizing the tissue-engineered biological material with various imaging modalities such as ultrasound. While a rectangular base is preferred as the shape of the chamber, the base is not limited to such a shape, and may reasonable encompass various shapes. Preferably, the size of the chamber is 1.3 inches in width, 3.0 inches in height, and 4.1 inches in length, however, may reasonably encompass various sizes that would allow the replication of the intended body function during testing and evaluation.

To prevent contamination of the test and evaluation environment, the housing chamber is hermetically sealed. This may be accomplished by providing the housing with a cover or lid which is connected thereto. A seal such as a rubber O-ring may also be provided. Preferably, the cover is connected to the chamber via a plurality of screws composed preferably of a thermoplastic or like material. However, the cover may be provided with external threads which cooperate with internal threads of the chamber in order to provide a rotateable connection between the lid and chamber.

Located at opposing surfaces of the housing chamber is a first set of inlet and outlet ports to permit fluid communication between the housing and the main fluid circuit. Preferably, the first set of inlet and outlet ports are a pair of $\frac{3}{8} \times \frac{3}{8}$ inches, straight barbed polycarbonate plastic connectors which are embedded in silicon and back filled in acrylic resin. In an exemplary embodiment of the invention, the connectors are offset at a 10–20 degree angle relative to the base of the chamber to allow for optimal ultrasound probe access. Moreover, the housing chamber includes a second set of inlet and outlet ports to permit fluid communication between the housing and a second auxiliary fluid circuit. The second set of inlet and outlet ports are preferably ¼ inch, straight barbed connectors which are also embedded in silicon and back-filled in acrylic resin.

In this embodiment, a tissue-engineered biological material, such as a semilunar heart valve scaffold is mounted in the housing chamber using polystyrene collars which are attached to the distal ends of the semilunar heart valve scaffold using rubber "O" rings of appropriate size to prevent leakage of cell culture media at each end of the construct while in the chamber. The tissue-engineered valve/collar construct will be interposed between the first inlet port and the first outlet port via a support mechanism comprising silicon tubing.

As previously mentioned, the pressure mechanism such as a pump may be placed in direct electronic communication with a control device such as a computer in order to generate predetermined or programmable pressure waveforms and flow through the circuit during systole. The computer may include an input device and an output device such as a display device. Input devices can include a mouse, a keyboard or the like, while the output device is preferably a display device such as a monitor or a liquid crystal display (LCD) screen. The computer is also capable of adjustably controlling the programmable pressure at a level which simulates or replicates intraluminal flow. This feature is advantageous since the intraluminal flow of said fluid through the main fluid circuit hemodynamically conditions the semilunar valve prior to in vivo implantation.

Located on the efferent arm of the main fluid circuit is a resistance device for generating pressure counter to the pressure generated by the pressure mechanism. The resistance device operates so as to simulate aortic pressure. Preferably, the resistance device is an afterload device or the like, specifically, any device added to the main fluid circuit that is capable of increasing the afterload in the apparatus. In essence, the afterload device increases the resistance in the main fluid circuit located downstream of the tissue engineered construct, and thus, increases the pressure throughout the apparatus. Such a device is manufactured by Harvard Apparatus, Mass. A section of the efferent arm of the main circuit is composed of tubing having an elastic recoil that acts to simulate the aorta and produce an afterload characteristic similar to what is found in vivo.

An oxygenator is also placed on the efferent arm of the main fluid circuit. The oxygenator functions to store the fluid media and conduct an oxygen-carbon dioxide gas exchange with the fluid media. Temperature regulation may occur by causing the fluid media to flow through a heat exchanger which is placed in series with the oxygenator to exchange heat through at least one of metal or plastic interfaces between the fluid media and a temperature-controlled fluid such as water.

In order to evaluate pressure of fluid flow within the fluid circuits, a plurality of in-line pressure data acquisition ports are provided on the afferent limbs of the fluid circuit. Preferably, the in-line pressure data acquisition ports are manufactured by Avecor Cardiovascular Inc., Minneapolis, Minn.

In accordance with the present invention, in fluid communication with the second auxiliary fluid circuit is an accessible closed bag compliance reservoir. The accessible closed bag compliance chamber is a compressible bag with elastic recoil that can essentially be of any size, and is accessible through stop-cock type ports. Any "soft-shell" bag or "hard shell" flask that acts as a reservoir for the fluid media, and a compliance chamber that permits radial expansion of the tissue engineered heart valve or blood vessel can be used and may be adapted from a standard ECMO circuit such as those manufactured by Avecor Cardiovascular Inc., Minneapolis, Minn. to allow for filling and emptying of the valve chamber.

To support metabolism of the living tissue of the heart valve, the fluid must contain certain nutrients. A cell culture medium, such as that produced by DMEM, Life Technologies, Grand Island, N.Y., is provided. The cell culture medium is supplemented with fetal bovine serum, L-glutamine, penicillin, streptomycin, such as those produced by Life Technologies, Grand Island, N.Y., and bFGF, such as that produced by Scios international, Calif. The cell culture medium and additives are chosen depending on the cell type that is used. Because tissue-engineered valves may be produced from a variety of different cell types, and in this regard, the invention can support the use of any appropriate cell culture medium type.

In accordance to another embodiment, a method is provided for evaluating the structure and function of a tissue-engineered semilunar valve or vascular graft under sterile conditions prior to in vitro implantation in a ventricular outflow tract. The method comprises steps of providing a hermetically sealed environment for housing and supporting the semilunar valve, providing a main circuit for permitting flow of a fluid media through the base housing generating physiologic flow of said fluid media through said main fluid circuit at a predetermined pressure and time, adjustably controlling the predetermined pressure through said main fluid circuit to a level which simulates or replicates intraluminal flow and assessing valve function and intraluminal flow of said fluid media. The assessment step may involve assessing effective orifice area, transvalvular pressure gradient, area of regurgitant flow, leaflet dynamics, and leaflet energy expenditure throughout the cardiac cycle using ultrasonography techniques or any like imaging techniques which are known in the art. The assessment step may also involve assessing forward and regurgitant flow patterns, volumes, and velocities using magnetic resonance imaging techniques, or like imaging techniques which are known in the art.

DETAILED DESCRIPTION OF THE INVENTION

Figure 1:
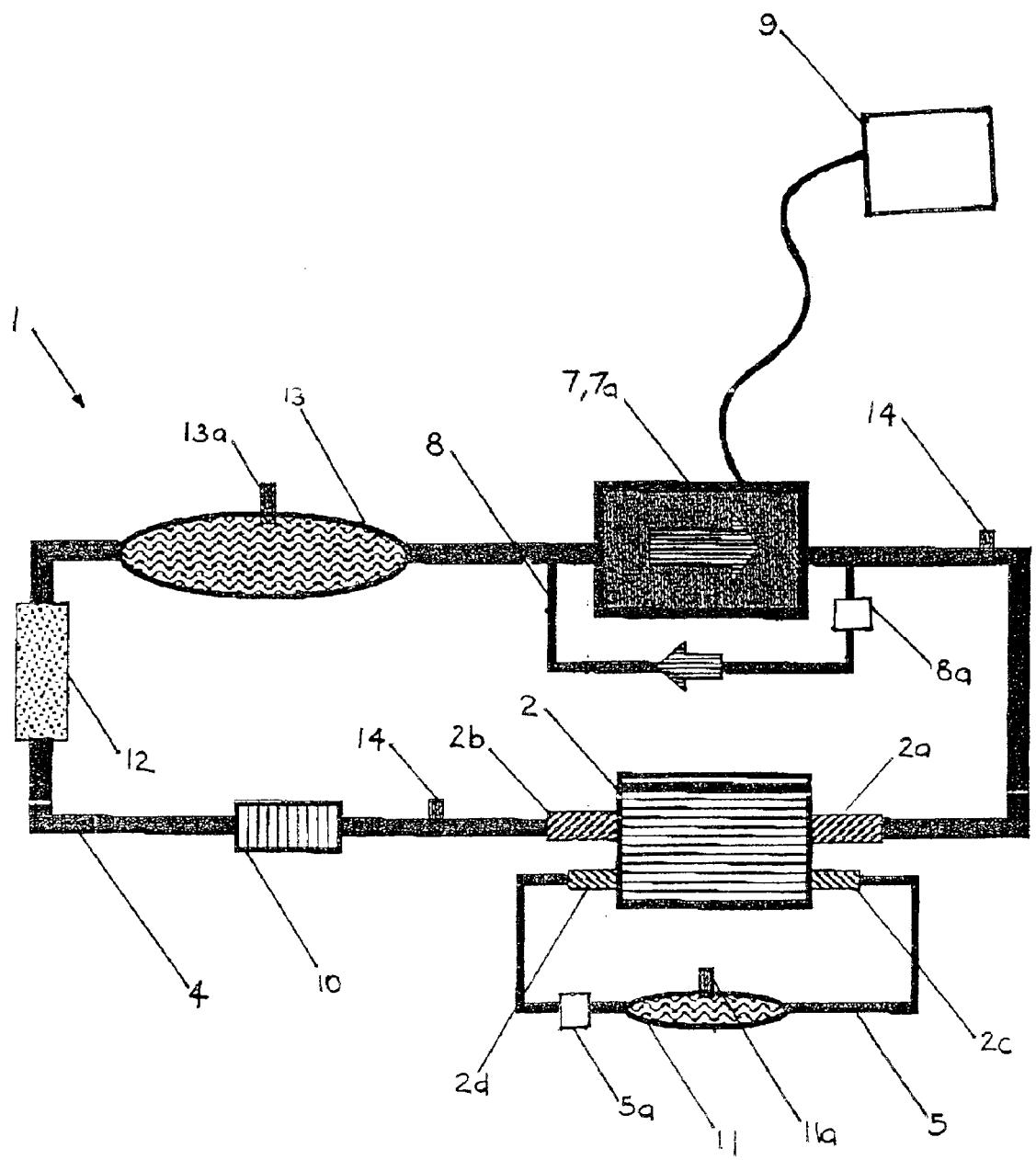
FIG. 1 is a schematic diagram of the apparatus for evaluating a structure and function of tissue-engineered valve prosthesis under sterile conditions.

Referring now to the drawings, in which FIG. 1 illustrates an apparatus 1 for evaluating the structure and function of laboratory-grown (i.e., tissue-engineered) three-dimensional biological material such as a semilunar valve or vascular graft 6 (FIG. 2) under sterile conditions prior to in vitro implantation of the semilunar valve/vascular graft in a ventricular outflow tract or in a peripheral vasculature to replace veins or arteries. The present inventors have developed a way to tissue-engineer in vitro a semilunar valved conduit for implantation in the right ventricular outflow tract of children. This involves the delivery of cells onto a biodegradable scaffold pre-shaped in an anatomical form that resembles the normal semilunar heart valve. The resulting cell-polymer construct is conditioned in the laboratory under mechanical forces which increase cell proliferation and extra cellular matrix (ECM) deposition. Following a 3-4 week in vitro valve conditioning period, the valve is implanted into the right ventricular outflow tract of a laboratory animal, and have been shown to function for a period of up to 20 weeks. Following the in vitro bio-conditioning period, however, only the structural properties of the tissue-engineered valve have been subjectively considered, and thus, the functional characteristics of the tissue engineered valve have been assumed.

Sterilization and the delivery of dissolved gases, nutrients and the removal of waste products of metabolism are necessary for a device that tests living autologous tissue-engineered valves when applying the tissue-engineered valve in a clinical setting, it becomes essential to demonstrate the structural integrity of the conduit wall and satisfactory function of the valve at the conclusion of the in vitro conditioning period. The wall of the conduit must remain in tact when subjected to under physiologic flow and pressure conditions, and overall function of the tissue-engineered valve must at least meet or surpass the functionality of conventional devices.

Figure 2:
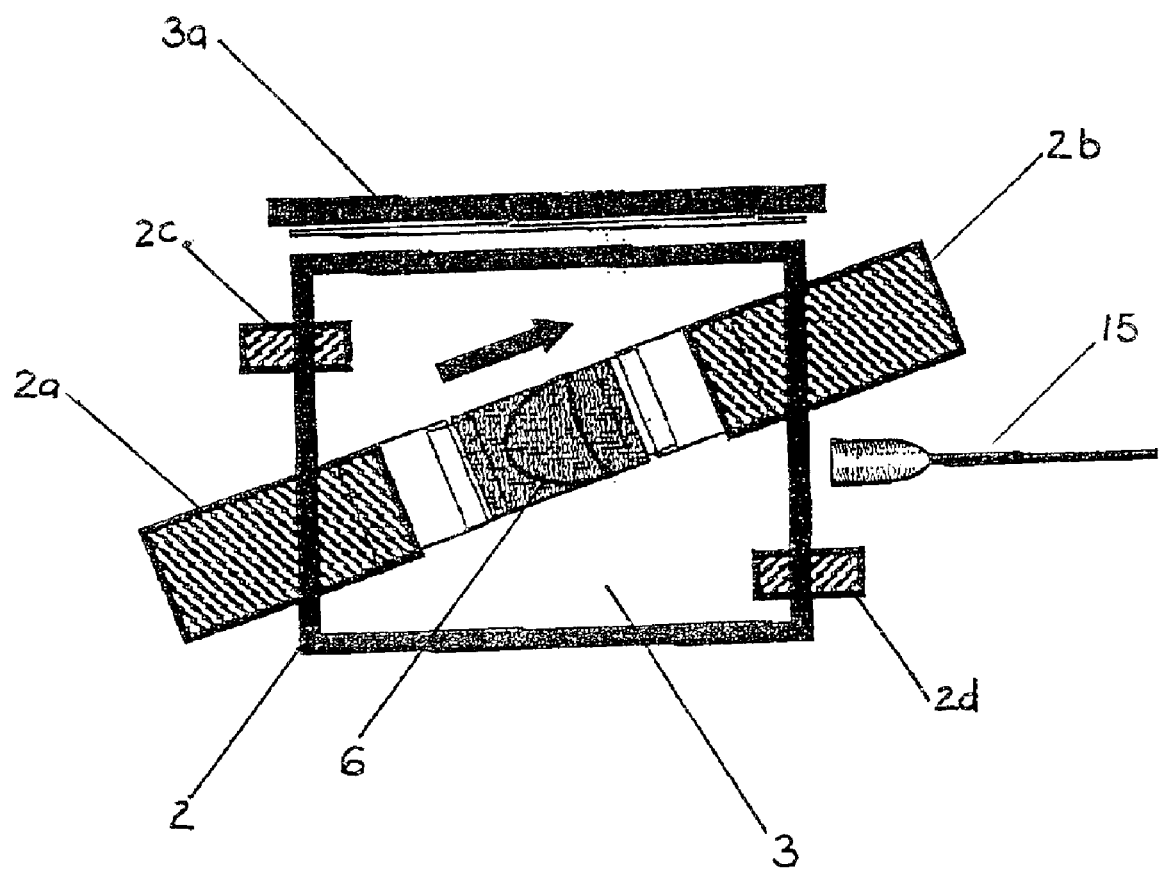
FIG. 2 is side view of a tissue-engineered valve interposed between first pair of inlet and outlet ports of the housing with an arrow depicting the direction of fluid flow.

In an exemplary embodiment of the invention, the apparatus 1 includes a hermetically sealed environment for housing and supporting the semilunar valve or vascular graft 6 (FIG. 2). The hermetically sealed environment includes a housing 2 and at least one annular chamber 3. Preferably, the housing 2 is a container having a base which comprises a transparent material that allows for the visualization of the tissue-engineered biological material in a test and evaluation environment. Preferably, a polymeric material such as clear acrylic manufactured is used for the housing 2. Acrylic is advantageous over other materials since it allows the capability of visualizing the semilunar valve or vascular graft 6 with using ultrasound technology such as an ultrasound probe 15. However, the housing 2 may be composed of any material that is both transparent and provides rigidity sufficient to withstand the various mechanical and operational forces which occur during testing and evaluation of the apparatus 1.

As shown in FIG. 1, while the housing 2 has an essentially rectangular shape in a preferred embodiment, the housing 2 is not limited to such a shape, and may encompass various shapes and configurations. In a preferred embodiment, the spatial dimensions of the housing 2 is 1.3 inches in width, 3.0 inches in height, and 4.1 inches in length. However, the housing 2 may encompass various sizes that would allow for optimum replication of the intended body function during testing. Moreover, the housing 2 includes a first pair of inlet/afferent and outlet/efferent ports 2a, 2b and a second pair of inlet/afferent and outlet/efferent ports 2c, 2d, which will be further described hereinbelow.

The housing 2 further includes a device for mounting or supporting a biological material such as a semilunar valve or vascular graft 6, the support permitting the biological material to be tested and evaluated while positioned in the chamber 3. The semilunar valve or vascular graft construct 6 is mounted in the chamber 3 using any well known technique, such as polystyrene collars which are mounted or attached to the distal ends of the semilunar valve 6 using rubber "O" rings of appropriate size. The semilunar valve 6 is interposed between the first inlet and outlet ports 2a, 2b of the housing 2 of using, preferably, silicon tubing. Preferably, the fluid circuit is composed of a compliant material such as polyvinyl chloride (PVC) tubing which connects the various components of the system.

In order to maintain the sterility of the environment in which the valve is placed, the chamber 3 is hermetically sealed using a cover 3a. The cover 3a is composed of the same material chosen for the housing 2, and thus, a polymeric material such as clear acrylic manufactured is preferably used. However, the cover 3a may comprise of any material that is transparent and provides rigidity sufficient to withstand the various mechanical and operational forces which occur during testing and evaluation of the apparatus 1. Preferably, the lid cover is connected to the housing 2 via a plurality of screws composed preferably of a thermoplastic or like material. However, the lid 3a may be provided with external threads which cooperate with internal threads of the housing 2 in order to provide a rotateable connection between the cover 3a and housing 2. In addition, an O-ring composed of an elastic polymeric material such as rubber may be provided to maintain the seal-tight relationship between the cover 3a and the housing 2.

The apparatus 1 further includes a main fluid circuit or conduit 4 which is in fluid communication with the housing 2. The main fluid circuit 4 serves to permit flow of a fluid media through the housing 2 and is connected thereto via the first pair of inlet/afferent and outlet/efferent ports 2a, 2b of the housing chamber 2. Preferably, the inlet 2a and outlet 2b ports are 3/8 inch×3/8 inch straight barbed polycarbonate connectors which are embedded in silicon and back filled in acrylic resin. It also preferred that the connectors are offset at a 10–20 degree angle relative to the base of the chamber 2 to allow for optimal ultrasound probe 15 access. Preferably, the main fluid circuit 4 comprises a rigid tubular polymeric material, such as polyvinyl chloride (PVC), which is in fluid communication with the various components of the apparatus. However, the main fluid circuit 4 is not limited to the use of PVC, and of course, may comprise any material suitable for optimizing the testing and evaluation of the biological material. A portion of the efferent limb of the main circuit 4 which is distal to the tissue engineered construct is composed of compliant tubing having elastic recoil to better replicate the afterload characteristics found in vivo.

In addition, a first auxiliary fluid circuit or conduit 5 is placed in fluid communication with the housing 2. The first auxiliary fluid circuit 5 serves to bypass the flow of the fluid media from the main fluid circuit 4 to thereby allow regurgitant flow of the fluid media within the main fluid circuit 4. The first auxiliary fluid circuit 5 is connected to the housing 2 via the second pair of inlet/afferent and outlet/efferent ports 2c, 2d of the housing chamber 2. Preferably, the second pair of inlet 2c and outlet 2d ports comprise 1/4 in.×1/4 in., straight barbed connectors and are embedded in silicon and back-filled in acrylic resin. It is also preferred that the first auxiliary fluid circuit 5 includes a check valve 5a for allowing unidirectional flow through the auxiliary fluid circuit 5. While the first auxiliary fluid circuit 5 preferably comprises a rigid tubular polymeric material such as polyvinyl chloride (PVC), the first auxiliary fluid circuit 5 is not limited to the use of PVC, and of course, may comprise any material suitable for optimizing the testing and evaluation of the biological material.

The system 1 includes pressure device 7 for generating physiologic flow of the fluid media through the main fluid circuit 4. The pressure device 7 is fluidically connected to the chamber 2 on the efferent arm of the main fluid circuit 4, i.e., proximal to first inlet port 2a of the housing 2. The pressure device 7 preferably is a pump such as a piston-driven pump, however, depending on the purpose for creating flow through a tissue engineered heart valve and/or blood vessel, any type of pump can be used. However, it is advantageous to use a pump that is capable of most closely simulating in vivo hemodynamic flow and pressure conditions. Hence, for this purpose, it is preferred that a bellows-type fluid pump is used.

In a preferred embodiment of the invention, the pump 7 is provided with a check valve 7a for preventing backflow of fluid in the system during the diastole. A second auxiliary or bypass circuit 8 with a check valve 8a is positioned to bypass the pump 7 and accommodate flow in the opposite direction in instances of flow regurgitation through the pressure means 7. The check valve 8a prevents backflow of the fluid media in the second auxiliary circuit 8 during diastole.

The pressure means 7 may be in electronic communication with a terminal device, i.e., a control device such as a computer or controller 9. In this regard, the controller 9 may include an input device (not shown) and an output device such as a display device (not shown). Input devices can be a mouse, a keyboard or the like, while the output device is preferably a display device such as a monitor or a liquid crystal display (LCD) screen. Of course, other input and output devices can also be used in accordance with the present invention. In this regard, the operation of the pump 7 is controlled by the controller 9 to generate predetermined (i.e., programmable) pressure waveforms and flow through the circuit 4 during systole. The controller 9 is also capable of adjustably controlling the predetermined pressure at a predetermined time period and at a level which simulates or replicates intraluminal flow. This is advantageous since the intraluminal flow of said fluid through the main fluid circuit 4 hemodynamically conditions the semilunar valve 6 prior to in vivo implantation. It will become apparent to those skilled in the art that practice of the invention may take place such the pump is not in direct electronic communication externally with a control device.

As shown in FIG. 1, located on the efferent arm of the main fluid circuit 4 is a resistance device 10 for generating pressure counter to the pressure generated by the pressure means 7, and thus, simulates or replicates aortic pressure. Preferably, the resistance device 10 is an afterload device, or any device added to the main fluid circuit 4 which is capable of increasing the afterload throughout the main fluid circuit 4. In essence, the afterload device increases the resistance in the main fluid circuit 4 located distal to the semilunar valve 6, and thus, increases the pressure throughout the apparatus.

In fluid communication with the second auxiliary fluid circuit is an accessible closed bag or "hard shell" compliance reservoir 11. Preferably, the accessible closed bag compliance reservoir 11 is a compressible bag, of essentially be of any size. Any "soft-shell" bag or "hard shell" flask that acts as a reservoir for the fluid media, and a compliance chamber that permits the radial expansion of the tissue engineered biological material such as a heart valve or blood vessel can be used to allow for filling and emptying of the valve chamber. In accordance to an exemplary embodiment, the accessible closed bag or "hard shell" compliance reservoir 11 may be accessible through stop-cock type ports 11a.

An oxygenator 12 is also placed on the efferent arm of the main fluid circuit. The principal function of the oxygenator 12 is to store the fluid media blood and conduct an oxygen-carbon dioxide gas exchange with the fluid media. Temperature regulation may occur by causing the fluid media to flow through a heat exchanger in which a heat exchange takes place through metal or plastic interfaces between the fluid media and a temperature-controlled fluid such as water.

Air is aspirated from an accessible in-line closed bag or "hard shell" reservoir 13 which is placed in fluid communication with the efferent arm of the main fluid circuit 4. Preferably, the accessible in-line closed bag reservoir 13 is a compressible container or the like composed of a material such as plastic. Essentially, the accessible in-line close bag or "hard shell" reservoir 13 can be of any size, and may be accessible through stop-cock type ports 13a. Any "soft-shell" bag or "hard shell" flask that acts as a reservoir for the fluid media can be used. In order to evaluate pressure of fluid flow within the fluid circuits 4, 5, 8, a plurality of in-line pressure data acquisition ports 14 are provided. Preferably, the in-line pressure data acquisition ports 14 are placed at various locations on the afferent and efferent limbs of the main fluid circuit 4.

To support metabolism of the living tissue of the semilunar valve 6, the fluid media must contain certain nutrients. A cell culture medium, such as that produced by DMEM, Life Technologies, Grand Island, N.Y., is provided. The cell culture medium is supplemented with fetal bovine serum, L-glutamine, penicillin, streptomycin, such as those produced by Life Technologies, Grand Island, N.Y., and bFGF, such as that produced by Scios international, CA. The cell culture medium and additives are chosen depending on the cell type that is used. Because tissue-engineered valves may be produced from a variety of different cell types, and in this regard, the invention can support the use of any appropriate cell culture medium type.

Figure 3:
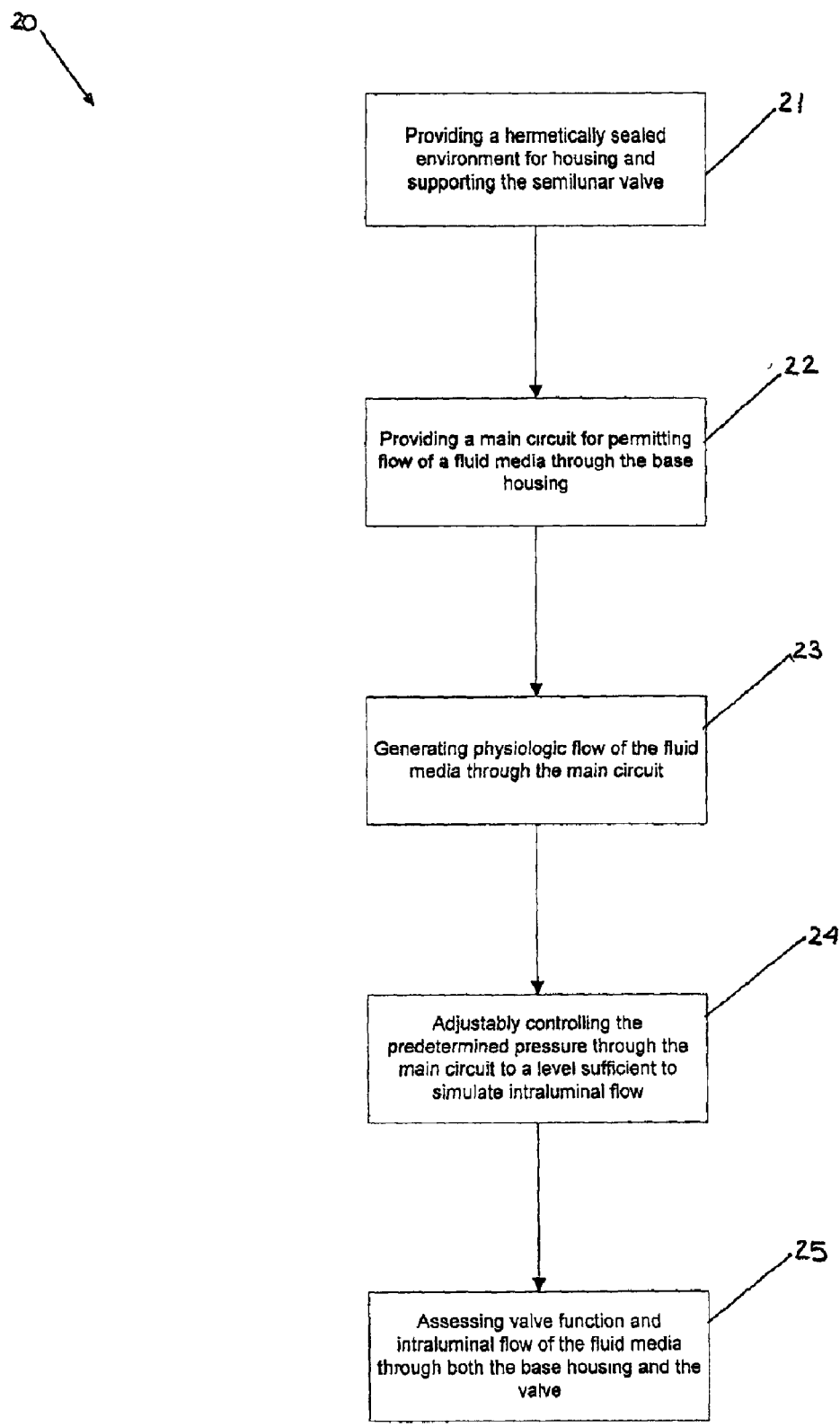
FIG. 3 is a flow diagram of the method of evaluating the structure and function of a tissue-engineered semilunar valve or vascular graft.

FIG. 3 shows a flowchart describing a method 20 in accordance with an embodiment of the invention for evaluating the structure and function of a tissue-engineered semilunar valve or vascular graft under sterile conditions prior to in vitro implantation in a ventricular outflow tract. Step 21 requires providing a hermetically sealed environment for housing and supporting the semilunar valve. As previously mentioned in the description of the system, the hermetically sealed environment may include a base, for housing and supporting the semilunar valve. Again, the base may a housing having an inlet port and an outlet port for allowing the flow of a fluid throughout the base. Step 22 requires providing a main circuit for permitting flow of a fluid media through the base housing.

In step 23, physiologic flow of the fluid media is generated through the main circuit. In an exemplary embodiment, the flow may be produced using a pressure means such as a pump. In particular, the pump may be of piston-driven type. Preferably, the flow generated by the pressure means is at a predetermined pressure and time. In step 24, the predetermined pressure is adjustably controlled through the main circuit to a level sufficient to simulate intraluminal flow. This intraluminal flow acts to hemodynamically condition the semilunar valve prior to in vivo implantation of said fluid through said main fluid circuit.

Finally, step 25 requires assessing valve function and intraluminal flow of the fluid media through both the base housing and the valve. The assessment step 25 may involve assessing effective orifice area, transvalvular pressure gradient, area of regurgitant flow, leaflet dynamics, and leaflet energy expenditure throughout the cardiac cycle using ultrasonography techniques or any like imaging techniques which are known in the art. The assessment step 25 may also involve assessing forward and regurgitant flow patterns, volumes, and velocities using magnetic resonance imaging techniques, or like imaging techniques which are known in the art.

Although exemplary embodiments of the present invention have been described in detail herein, it should be appreciated by those skilled in the art that many modifications are possible without materially departing from the spirit and scope of the teachings and advantages which are described herein. Accordingly, all such modifications are intended to be included within the spirit and scope of the present invention as defined by the appended claims.

What is claimed is:

1. An apparatus for evaluating a structure and function of a tissue-engineered construct under sterile conditions, said apparatus comprising:

(a) a base for supporting the tissue-engineered construct, said base including a housing having an inlet port and an outlet port;

(b) a main fluid circuit for allowing flow of a fluid media through said housing, said main fluid circuit having an efferent section in fluid communication with said outlet port and an afferent section in fluid communication with said inlet port;

(c) pressure means in fluid communication with said main fluid circuit for generating physiologic flow of the fluid media through said main fluid circuit;

(d) resistance means in fluid communication with said main fluid circuit for replicating an afterload characteristic, said resistance means positioned distal to the tissue-engineered construct on said efferent section of said main circuit;

(e) compressible container placed in fluid communication with said housing for allowing radial movement of the said tissue-engineered construct during the flow of said fluid media through said main fluid circuit; and (f) control means in electronic communication with said pressure means for adjustably controlling the pressure of the fluid media in said main fluid circuit at a level which replicates intraluminal flow, wherein said intraluminal flow of said fluid through said main fluid circuit hemodynamically conditions the tissue-engineered construct prior to in vivo implantation in a ventricular outflow tract.

2. The apparatus according to claim 1, wherein said container comprises a closed bag compliance reservoir.

* * * * *